US 6,544,794 B1

(12) United States Patent
Denda

(10) Patent No.: US 6,544,794 B1
(45) Date of Patent: Apr. 8, 2003

(54) METHOD FOR VISUAL IMAGING OF ION DISTRIBUTION IN TISSUE

(75) Inventor: Mitsuhiro Denda, Yokohama (JP)

(73) Assignee: Shiseido Company, Ltd., Tokyo (JP)

( * ) Notice: Subject to any disclaimer, the term of this patent is extended or adjusted under 35 U.S.C. 154(b) by 0 days.

(21) Appl. No.: 09/570,447

(22) Filed: May 12, 2000

(51) Int. Cl.$^7$ .............................................. G01A 37/00
(52) U.S. Cl. ............................. 436/56; 436/79; 436/63; 436/81; 436/124; 436/172; 422/82.08
(58) Field of Search .................. 422/82.08; 436/56, 436/63, 79, 81, 124, 172

(56) References Cited

U.S. PATENT DOCUMENTS 5,494,802 A * 2/1996 Watanabe et al. ............ 435/7.1

OTHER PUBLICATIONS

"Visual Imaging of Ion Distribution in Human Epidermis", Biochemical And Biophysical Research Communications, vol. 272, No. 1, pp. 134–137, May 2000.

* cited by examiner

*Primary Examiner*—Lyle A. Alexander
(74) *Attorney, Agent, or Firm*—Townsend & Banta

(57) ABSTRACT

A method is provided for producing a visual image of ions in a thin frozen tissue sample by placing the tissue sample in contact with a thin membrane having a water soluble gel or hydrophobic plastic thin film which has incorporated in or placed on its surface a fluorescent or color ion indicator which fluoresces or changes color under light of a particular wavelength. The thin frozen tissue sample is then subjected to light having a wavelength to cause the ion indicator to fluoresce or change color.

18 Claims, 6 Drawing Sheets

METHOD FOR VISUAL IMAGING OF ION DISTRIBUTION IN TISSUE

BACKGROUND OF THE INVENTION

The present invention relates in general to visual imaging of the ion distribution in tissue and, more particularly, to a method of producing visual images of ion distribution in human epidermis. The method of this invention can provide an extremely inexpensive and simple method to detect ion distribution compared with the prior art methods.

PRIOR ART

Studies suggest that ionic signals such as calcium and potassium play an important role in the homeostatic mechanism of the epidermal barrier function. Observation of these ions would provide important information to understand epidermal homeostasis. However, image analysis of ions in the skin is technically difficult. Previously, the distribution of calcium and potassium has been studied by electron microscopic analysis after calcium precipitation or by Particle Induced X-Ray Emission (PIXE) analysis of the skin. Although the results of these procedures provides important quantitative information, some other important elements such as hydrogen or magnesium, could not be observed by these methods because of their low atomic weight. Moreover, since these methods require dehydration or fixation of the sample without destroying the native chemical composition, they require complicated processes.

Secondary ion MS (SIMS)-based imaging technique also can be used for observation of intercellular elements. But this method also requires freeze-dry processing of the sample to be analyzed.

Although frozen hydrated and frozen freeze-dried sample preparations do provide optimal samples for SIMS analysis, neither approach preserves the living-state cell matrix. In frozen hydrated samples, the physical form of the cellular water is completely altered, and, in freeze-drying, the water is removed from the specimen. The choice between frozen hydrated and frozen freeze-dried sample preparations may depend on the type of SIMS analysis desired. The frozen hydrated analysis is preferred for static time-of-flight molecular imaging. Static SIMS experiments have also imaged molecules in tissue sections after air drying. On the other hand, frozen freeze-dried sample preparations are preferred in dynamic SIMS. Analysis of frozen hydrated cells under a dynamic primary beam preferentially removes water along the z-direction. This effect also enhances other analyte signals and causes false image contrasts in ion images. Additionally, frozen hydrated biological samples offer poor electrical conductivity, whereas conductivity is enhanced upon freeze-drying.

Further, freeze-drying may cause cell shrinkage and often damages some of the cellular morphology. To minimize this damage, sample freezing and freeze drying at low temperatures have been used. For example, morphological evaluations of fractured cells and membrane pieces prepared with a "sandwich fracture" method using electron and laser scanning confocal microscopic techniques, revealed well-preserved membrane particles, mitochondria, lysosomes, Golgi apparatus, and cell cytoskeleton. This is not surprising, because the method quick freezes cell monolayers of $\leq 10$ $\mu$m thickness and freeze-dries the sample at temperatures of $-80°$ C. or lower.

The presence of external cell growth medium complicates the direct analysis of cultured cells by ion microscopy. Washing out the nutrient medium can expose calls to a foreign solution that may perturb them and affect their ionic composition. These obstacles are overcome by using a sandwich freeze fracture method developed in our laboratory.

It is therefore an object of the present invention to provide a method of imaging ions in tissue samples without any substantial alteration of the native chemical composition of the cell by an expensive and simple procedure.

SUMMARY OF THE INVENTION

A method is provided according to the present invention of producing a visual image of ions in tissue samples which comprises placing frozen thin tissue sample in contact with a thin membrane formed from a water soluble polymer gel or hydrophobic plastic film having incorporated in or placed thereon a fluorescent or color ion indicator which fluoresces or changes color under light of a particular wavelength. The thin frozen tissue sample is then subjected to light of a wavelength to cause the ion indicator to fluoresce or change color.

DETAILED DESCRIPTION OF THE INVENTION

In a preferred method of the present invention, the tissue sample to be analyzed is a frozen tissue sample of human skin. The human skin sample can be any portion of the skin, but it is preferred that it is the epidermal layer and dermal layer, etc. The sample size is not limited and suitable sample size can be easily determined in any particular test. In a preferred embodiment the sample size is approximately 1 mm×1 mm cross-section tissue sample. However, the size of the tissue sample may be dictated by the type of equipment used in photographing and irradiating the tissue sample. In one embodiment of the invention, a cross-section of the skin can be analyzed by cutting the skin sample with a cryostat to a thickness of about 10 $\mu$m. Preferably, the frozen thin tissue sample is cut to a thickness of from about 5 to 10 $\mu$m for use in a fluorescence microscope.

According to a preferred method of the present invention, the frozen thin tissue sample is brought into contact with a thin membrane of a water soluble polymer gel or hydrophobic plastic film. Preferably, the water soluble polymer used to form the plastic film is a polymer selected from the group consisting of polyacrylamide, polyvinyl alcohol, or polysaccharide which is gelated or solidified into sheet form by cross bridging or drying, or crosslinking or polymerization of a monomer.

When the membrane comprises a water soluble polymer gel such as polysaccharide, the membrane preferably comprises from about 2 wt % of said polymer and about 98% of water. The content of said polymer and water depends on the particular polymer being used to form the membrane. According to the present invention, the membrane upon which the tissue sample is placed forms a three-dimensional structure which prevents any substantial water flow inside the structure so as to prevent any substantial movement of an ion indicator in the membrane.

Incorporated in or placed in the thin membrane is a fluorescent or color ion probe which fluoresces or changes color under light of a particular wavelength. The concentration of the ion probe is not limited but is preferred to use about 10 $\mu$g/ml based on the membrane being used.

In the process of the present invention for producing visual images of ions in tissue samples, any of the conventional ion probes can be used for the detection of any ions. For example, calcium ion probes can be used as described in a Japanese non-examined patent publication Tokkai HEI 2-28542. Other suitable ion probes for calcium available from Molecular Probe of Eugene, Oreg. USA include Fura-2 (5-Oxazolecarboxylic acid, 2-(6-(bis(carboxymethyl) amino)-5-(2-(2-(bis(carboxymethyl)amino)-5-methylphenoxy)ethoxy)-2-benzofuranyl)-, pentapotassium salt) Fluo-4. Preferred magnesium ion probes include Mag-Fura-2 (Oxazolecarboxylic acid, 2-[6-[bis(carboxymethyl) amino]-5-(carboxymethoxy)-2-benzofuranyl]-, tetrapotassium salt).

Preferred potassium ion probes include PBFI(1,3-Benzenedicarboxylic acid, 4,4'-[1,4,10,13-tetraoxa-7,16-diazacyclooctadecane-7,16-diylbis(5-methoxy-6,2-benzofurandiyl)]bis-,tetraanimonium salt). For example, sodium ion probes include SBFI(1,3-Benzenedicarboxylic acid, 4,4'-[1,4,10-trioxa-7,13-diazacyclopentadecane-7,13-diylbis(5-methoxy-6,2-benzofurandiyl)]bis-, tetraammonium salt). Also, zinc ion probes, for example, include TSQ(N-(6-methoxy-8-quinolyl)-p-toluenesulfonamide). Suitable chloride ion probes, for example, include MEQ(6-methoxy-N-ethylquinolinium iodide). Suitable ion probes for reactive oxygen include, for example, carboxy -H2DCFDA (5-(and-6)-carboxy-2',7'-dichlorodihydrofluorescein diacetate), and suitable lipid ion probes include, for example, Dil (1,1'-dioctadecyl-3,3,3',3'-tetramethylindocarbocyanine perchiorate).

Among preferred probes are Calcium Green-1; AM ester (C-3011); Magnesium Green, AM ester (M-3735); PBFI, AM ester (P-1266); Sodium Green (S-6900); Newport Green (N-7990); Potassium probe PBFI; Chloride Probes 6-Methoxy-N-(3-sulfopropyl)quinolinium (SPQ, M-440), N-(Ethoxycarbonylmethyl)-6-methoxyquinolinium bromide (MQAE, E-3101), 6-Methoxy-N-ethylquinolinium iodide (MEQ, M-6886), and Lucigenin (L-6868); Membrane potential, JC-1 (T-3168), JC-9 (D-22421), and Dil, DiO, DiD,-General purpose fluorescent membrane stains, all of which can be obtained from Molecular Probes, Inc. of Eugene, Oreg., USA.

Preferred molecular probes for singlet oxygen include trans-1-(2'-methoxyvinyl)pyrene available from Molecular Probes of Eugene, Oreg. In addition, zinc probes for detecting $Zn^{2+}$ include Newport Green, dipotassium salt, having the molecular formula $C_{30}H_{24}Cl_2K_2N_4O_6$. Suitable molecular probes for $Fe^{2+}$, $Cu^{2+}$ are Phen Green FL, dipotassium salt having the formula $C_{33}H_{18}K_2N_4O_5S$; suitable indicators for probes for $Mg^{2+}$ include Magnesium Green, pentapotassium salt, molecular formula $C_{33}H_{17}Cl_2K_5N_2O_{13}$; a preferred $CA^{2+}$ probe is Calcium Green-1, hexapotassium salt having a molecular formula of $C_{43}H_{27}Cl_2K_8N_3O_{16}$ and a preferred $Na^+$ molecular probe is Sodium Green, tetra (tetramethylammonium)salt having a molecular formula $C_{84}H_{100}Cl_7N_8O_{10}$, all of which are obtainable from Molecular Probes, Inc. of Eugene, Oreg.

The membrane for use in producing a visual image of ions in a tissue sample can be formed by first preparing an aqueous solution containing from about 5 to 20 wt % of polyacrylamide or polyvinyl alcohol or from about 0.05–2 wt % of polysaccharide together with an ion probe for the particular ion to be detected. A few drops of this aqueous solution can then be dripped on a glass slide which is preferably heated to a temperature of from about 40–50° C. to vaporize a portion of the water. Alternatively, an agarose gel can be formed from an aqueous solution dripped onto a glass slide and then dried to form a thin gel membrane. In a preferred embodiment the polysaccharide is gelated or solidified into sheet form by cross-bridging or drying, or crosslinking or polymerization of a monomer on a flat surface such as a glass slide so as to form a very thin membrane. According to a preferred method, the ion indicator is incorporated into the material forming the membrane before it is cast into a thin film. However, the ion probe can also be applied as a surface coating on the gel membrane.

After the thin frozen tissue sample is placed in contact with the thin membrane, the sample is then subjected to light of a wavelength to cause the ion probe to fluoresce or change color and the color change or fluorescence of the ion probes is observed by means of an optical microscope, fluorescent microscope, confocal microscope, and/or multiphoton laser scanning microscope.

BRIEF DESCRIPTION OF THE PHOTOGRAPHS

EXAMPLE

Figure 1A:
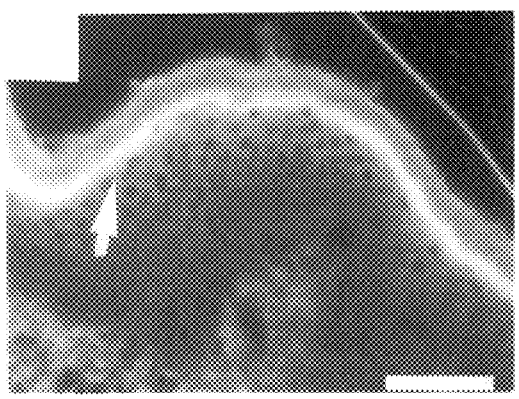
FIG. 1A is a photomicrograph of a normal skin epidermal granular layer showing the localization of calcium (white arrow)
Figure 1B:
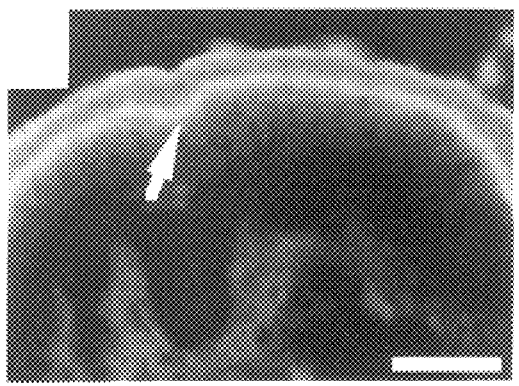
FIG. 1B is a photomicrograph of a normal skin epidermal granular layer showing the localization of magnesium before tape stripping (white arrow)
Figure 1C:
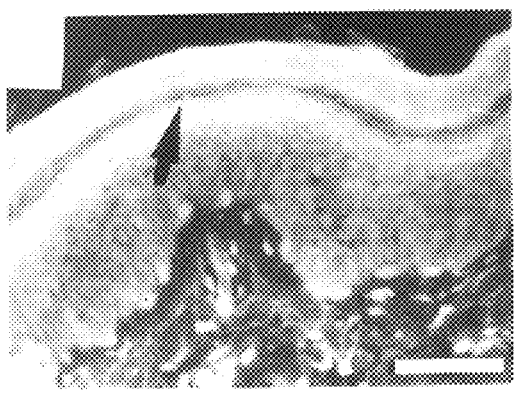
FIG. 1C is a photomicrograph of a normal skin epidermal granular layer showing the localization of potassium, and illustrating particularly that the concentration of potassium is highest in the spinous layer (black arrow) and the lowest in the granular layer before tape stripping.
Figure 1D:
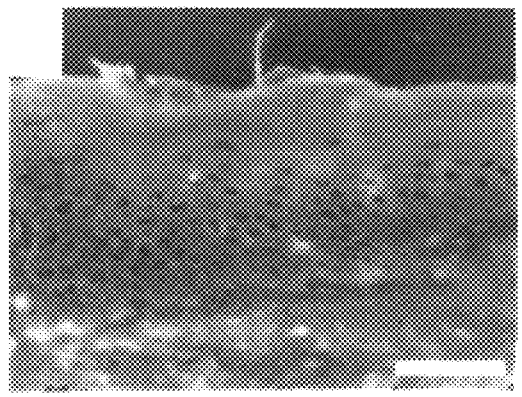
FIG. 1D is a photomicrograph of a normal skin epidermal granular layer showing the homogeneous distribution of sodium around the whole epidermis.
Figure 1E:
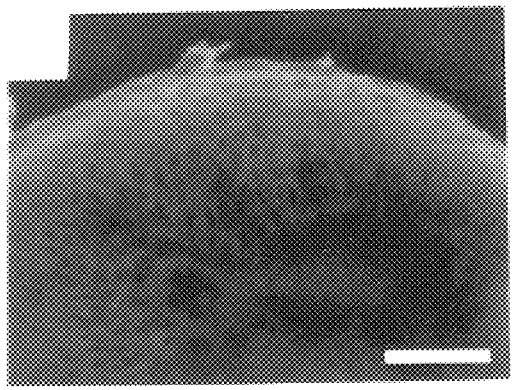
FIG. 1E is a photomicrograph showing the skin in FIG. 1A, taken thirty minutes after tape stripping, illustrating the disappearance of the calcium gradation.
Figure 1F:
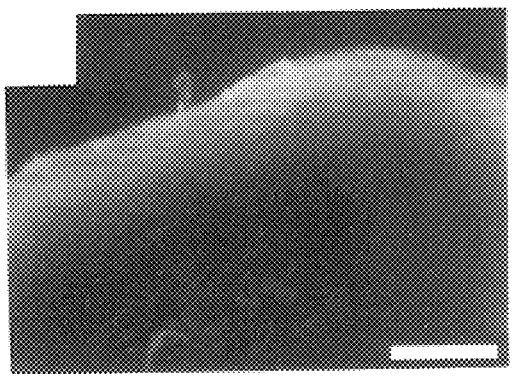
FIG. 1F is a photomicrograph showing the skin in FIG. 1B, taken thirty minutes after tape stripping, illustrating particularly the disappearance of the magnesium gradation.

The following example is exemplary only of the present invention. All percentages are in weight percent.

Example 1

A. Preparation Of Skin Tissue Sample

Skin samples were obtained from the inner forearm of healthy males who gave their informed consent by cutting with a Diener Spezial, CHR Diener (dissecting scissors). The samples were biopsied from untreated skin 30 minutes after tape stripping. To check the reproducability of results and avoid error, at least three samples were taken from one region. Tape stripping was carried out 20 times. At that time, most of the stratum corneum was removed. Samples were immediately frozen in an isopentane-filled metal jar which was kept in liquid nitrogen to prevent artifactual redistributions. These frozen samples were kept at −80° C. until sectioning.

B. Visualization And Imaging of Ions

Agarose powder (Type I-B; Shigma) is dissolved in about 90° C. water in a beaker and mixed on a hot plate. Thereafter, each of the ion probes described below was mixed in the solution while heating on a hot plate at about 50° C. to form a final Agarose gel with a concentration of 2%. Thereafter, a small portion of each of the mixtures containing different ion probes was spread to a depth of about 50 μm on slide glass to form a thin membrane on the glass. For the calcium observation, a final concentration of 10 μg/ml of calcium green 1 ion probe was mixed with the agarose gel before the formation of the membrane. For the magnesium observation, a final concentration of 10 μg/ml of Magnesium Green (produced by Molecular Probe, Inc.) and 0.2 mM final concentration of ethylene glycol bis(2-aminoethyl ether)-N,N,N',N'-tetraacetic acid (EGTA) were mixed together. For the potassium observation, the final concentration of 10 μg/ml of PBFI, referred to above, was mixed with the agarose gel. For the sodium observation, the final concentration of 10 μg/ml of sodium green was mixed with the agarose gel.

In the case of hydrogen ion (pH) observation, first an agarose gel membrane was formed and then 20 ml of 0.01% Bromocresol Green ethanol solution was spread over the gel membrane.

A frozen section of skin 10 μm in thickness prepared by Cryostat as described above, was then placed in contact with the gel membrane and within a couple of hours, the whole picture was taken. It is necessary to promptly photograph the tissue sample because within 12 hours after the preparation, the clear images disappeared. An Olympus microscope system (AH3-RFC, Olympus, Tokyo, Japan) was used for observation and photographing the tissue samples.

For Calcium Green 1, Magnesium Green, and Sodium Green (all molecular probes produced by Molecular Probe, Inc.), the wavelength of the excitation light for the ion probe was 546 nm. For the potassium indicator, PBFI, the wavelength of the excitation light was 334, 365 nm. For each of these observations, at least five sections were observed to find common features.

C. Results Of Imaging Ions

The images of calcium, magnesium, potassium and sodium in the skin are shown in FIG. 1. These are the representatives of each observation. In normal skin, calcium was localized in the epidermal granular layer (FIG. 1A). Thirty minutes after tape stripping, this gradation disappeared (FIG. 1E). Magnesium also showed the same tendency (FIG. 1B, F).

Figure 1G:
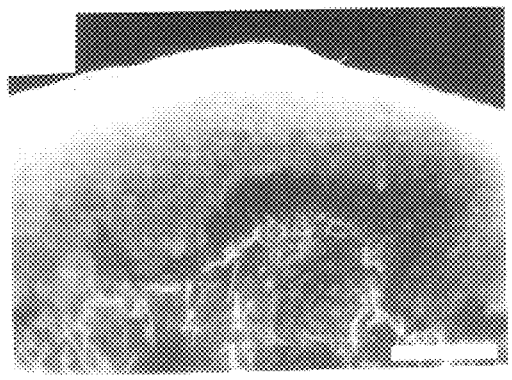
FIG. 1G is a photomicrograph of the skin in FIG. 1C, taken thirty minutes after tape stripping, illustrating the disappearance of the potassium gradient and the homogeneous distribution of the sodium around the whole epidermis by tape stripping.
Figure 1H:
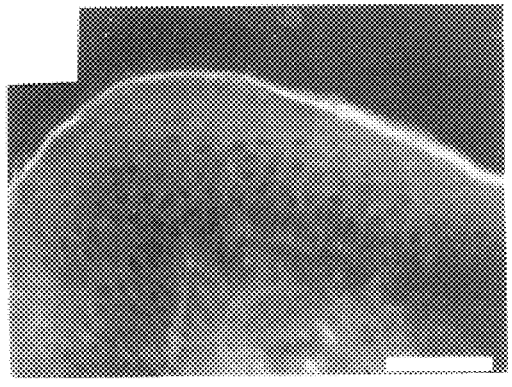
FIG. 1H is a photomicrograph of a normal skin epidermal granular layer in FIG. 1D, taken thirty minutes after tape stripping, illustrating the homogeneous distribution of sodium ion around the whole epidermis.
Figure 2A:
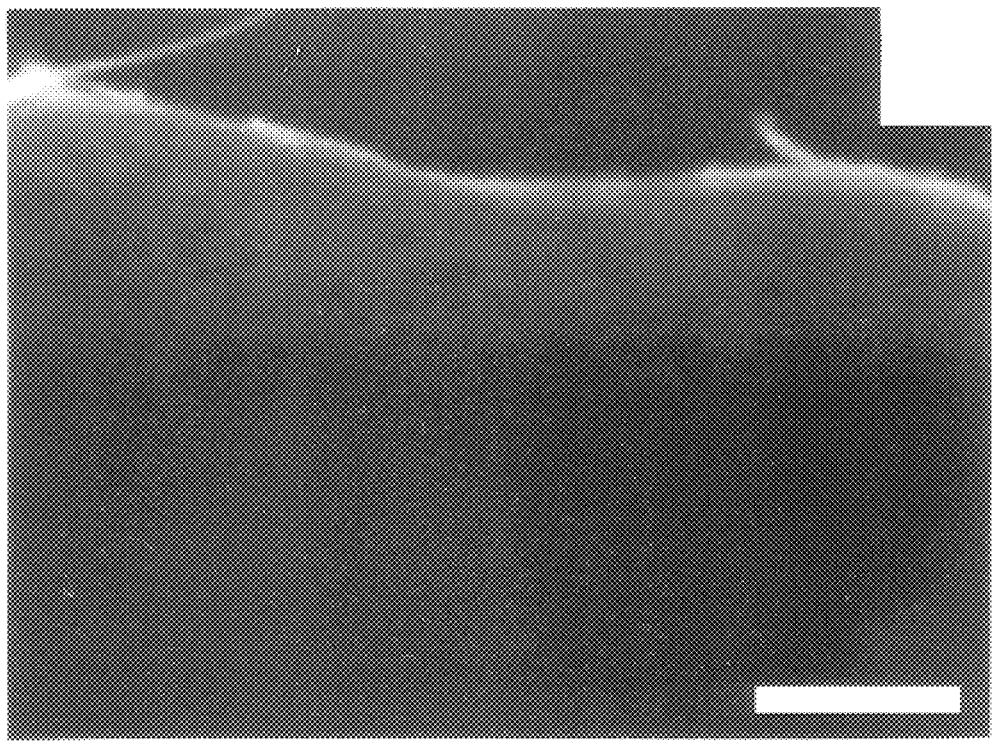
FIG. 2A is a photomicrograph of normal skin epidermal granular layer using calcium indicators, illustrating that EDTA absorbed the fluorescence of calcium indicator.

The concentration of potassium was the highest in the spinous layer and the lowest in the granular layer (FIG. C). This gradation also disappeared after tape stripping (FIG. 1G). Sodium showed a homogeneous distribution around the whole epidermis (FIG. 1G), which was not affected by tape stripping. To confirm these results, experiments were carried out with calcium or magnesium indicators using a 50 mM EDTA solution (FIG. 2A,B). EDTA absorbed most of the fluorescence in the epidermis. This indicates that the gradation in FIG. 1 showed the distribution of each ion.

Figure 3A:
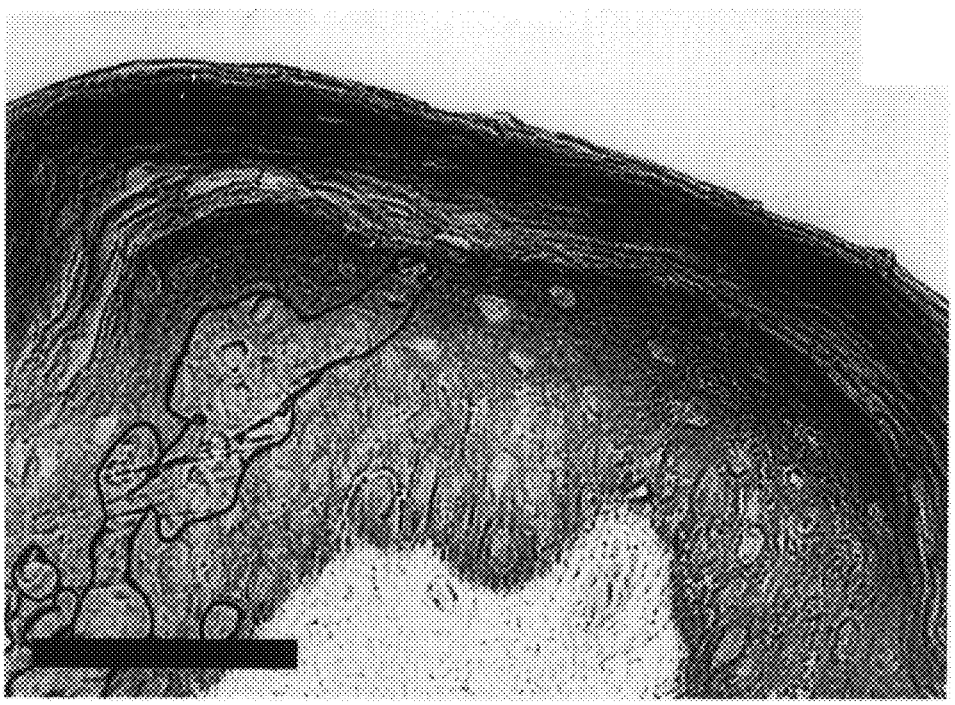
FIG. 3(A–B) is a photomicrograph of normal skin epidermal layer showing the gradation of pH in the skin before and after tape stripping.
Figure 3B:
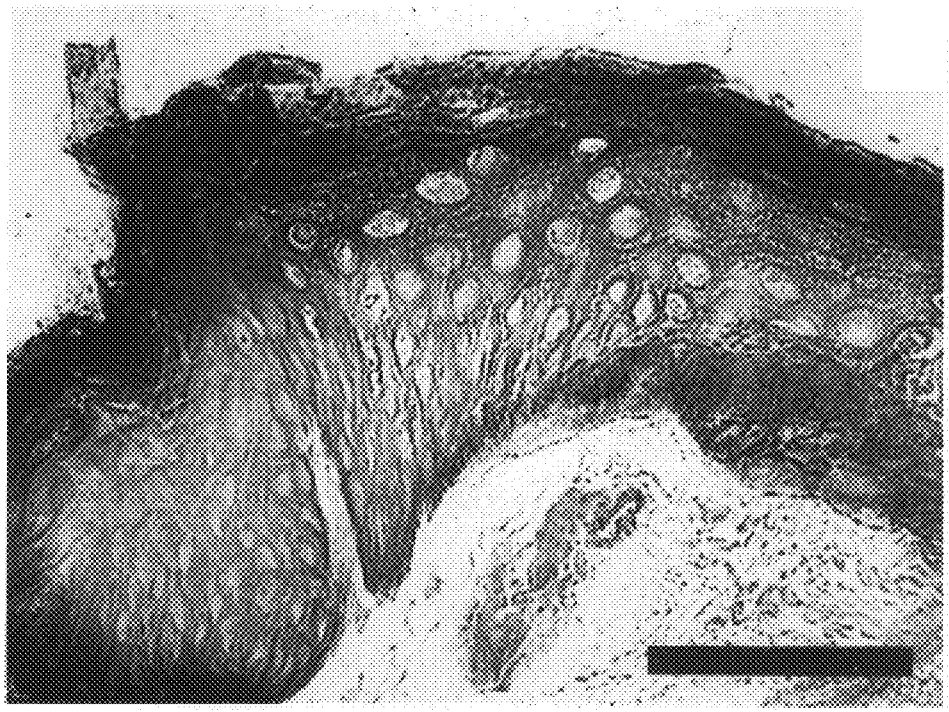
Figure 4A:
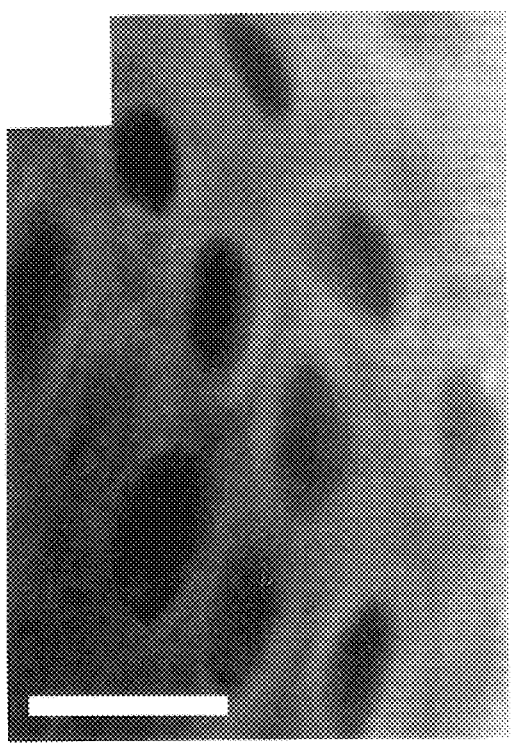
FIG. 4A is a photomicrograph at high magnification after tape stripping of the spinous layer of the epidermis, showing the calcium distribution.
Figure 4B:
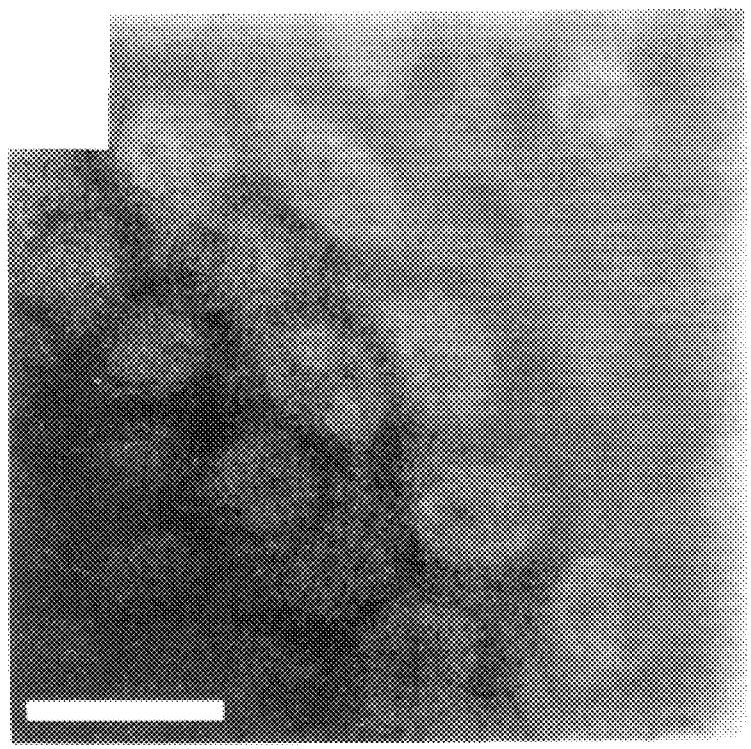
FIG. 4B is a photomicrograph at high magnification after tape stripping of the spinous layer of the epidermis showing the magnesium concentration was slightly higher in the nucleus.
Figure 4C:
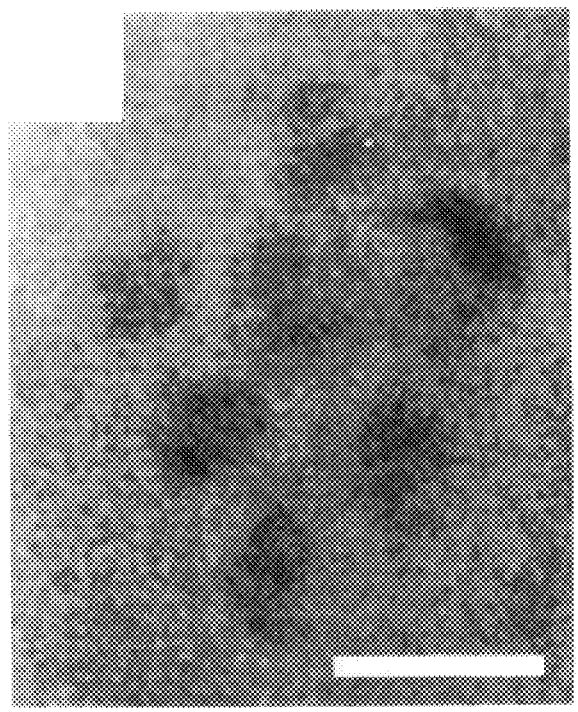
FIG. 4C is a photomicrograph at high magnification after tape stripping of the spinous layer of the epidermis, showing the potassium ions did not perform a clear distribution in the skin.
Figure 4D:
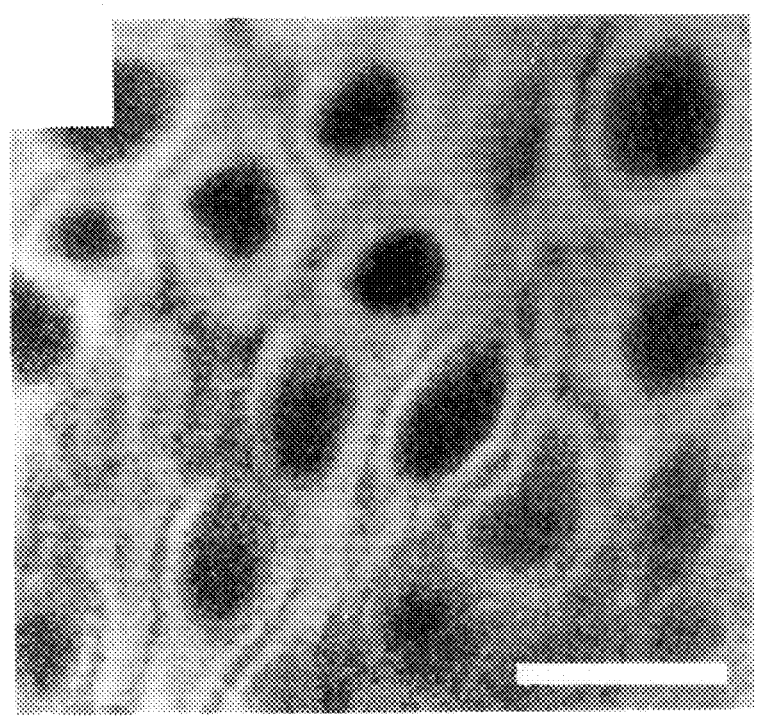
FIG. 4D is a photomicrograph at high magnification after tape stripping of the spinous layer of the epidermis, showing the sodium distribution.

The gradation of pH in the skin before and after tape stripping are shown in FIG. 3. In both cases, the stratum corneum and upper epidermis were more acidic (4.0–4.5 indicated by yellow-green). A deeper part of the epidermis and dermis were less acidic (higher than 5.6 indicated by blue-green). No obvious difference in pH gradation was observed after tape stripping.

Photographs of the spinous layer of the epidermis at a high magnification after tape stripping are shown in FIG. 4. Calcium (FIG. 4A) and sodium (FIG. 4D) distribution showed an obvious pattern. In both cases, these ions were absent in the nucleus. On the other hand, after tape stripping, the magnesium concentration was slightly higher in the nucleus (FIG. 4B). Potassium did not show a clear distribution pattern (FIG. 4C).

Discussion

A polymer gel, such as agarose or polyacrylamide, forms a three-dimensional structure and prevents any substantial water flow inside the structure. Therefore, this gel structure can be used for electrophoresis or in situ zymography. According to the present invention the diffusion of the chemical indicators may be prevented, and the agarose membrane shows the images of the ion distribution.

Ionized calcium is the most common signal transaction element.

In the normal epidermis, it has been found by the method of the present invention that the calcium concentration is higher in the upper epidermis, i.e., granular layer and lower in the deeper epidermis, i.e., basal layer. In the human study herein, the peak of calcium concentration in the epidermal granular layer became broad. These results suggest that calcium plays an important role in barrier homeostasis and/or signaling of barrier insults.

Figure 2B:
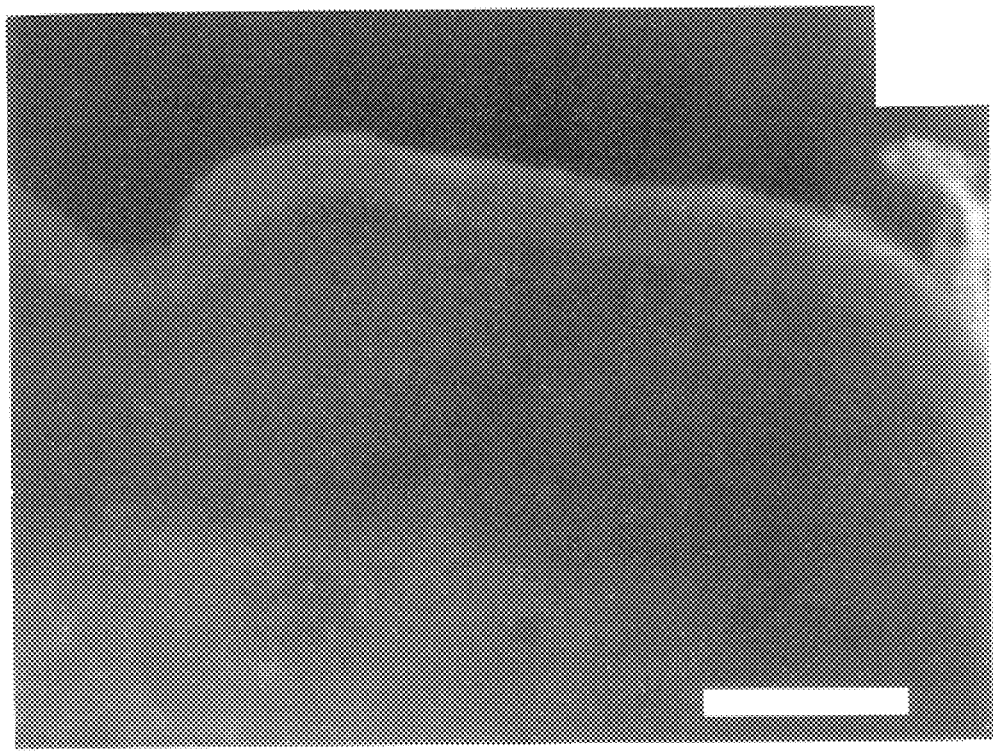
FIG. 2B is a photomicrograph of normal skin epidermal granular layer using magnesium indicator, illustrating that EDTA absorbed the fluorescence of magnesium indicator.

It has been found using the method of the present invention that there is a gradation in calcium in the epidermis (See FIG. 2b). Although the role of magnesium in the epidermis remains largely unknown, it is known that magnesium is required for the activity of Rab-geranylgeranyl transferase which modifies Rab. It has been previously demonstrated that application of magnesium after tape stripping accelerates barrier recovery. After the modification, Rab plays an important role on exocytosis and endocytosis. For the barrier formation, exocytosis of the lamellar body is an important process. Previous studies have indicated that Rab is modified by Rab-geranylgeranyl transferase during the terminal differentiation of the epidermis. It is believed that magnesium may be required in the differentiation of the keratinocyte or the barrier homeostasis.

Previously taken images of the skin suggest a close relation between potassium and calcium. Both ions play an important role in the terminal differentiation of keratinocyte or stratum corneum barrier function. Using the method of the present invention, potassium and calcium were localized comparably before and after barrier disruption. The disappearance of the potassium distribution in the present examples is similar to a previous study of hairless mice. The relative localization of these ions may be important for epidermal homeostasis.

The mechanism of the quick movement of calcium, magnesium and potassium after the barrier insult (barrier disruption by tape stripping) remains unknown. There is an electric potential between the surface (negative) and bottom (positive) of the skin. This potential is erased immediately by barrier disruption and with slow recovery. The skin surface potential may be induced by the distribution of the ions.

Using the method of the present invention, sodium did not show a gradation in the epidermis (See FIG. 4). The barrier insults did not affect the sodium ion distribution. This result suggests that sodium is not directly related to the cutaneous barrier homeostasis.

It can be seen from the results herein that localization in each cell was different between calcium and magnesium after barrier disruption. The concentration of calcium was low in the nucleus and relatively high in the cytosol. The concentrations of sodium in the cytosol was also higher than in the nucleus. On other hand, the magnesium concentration after tape stripping is slightly higher in the nucleus than in the cytosol. Magnesium ion has an ability to decrease the entropy of the water structure. Thus, magnesium plays a role to stabilize the nucleus protein structure. Magnesium may be important against environmental insults.

It is known that a lower pH in the upper epidermis would be important for barrier formation because lipid processing enzymes require it. Previously, application of basic buffer solution has been shown to delay the barrier recovery. The epidermis has a mechanism to keep the pH gradient for the barrier homeostasis. However, this gradation was not altered by barrier insults. The mechanism might be different from that of other divalent ions.

The ion profile has been reported to be altered in various skin diseases. For example, abnormal calcium distribution was observed in psoriatic epidermis and atopic dermatitis. The distribution of zinc and iron was also altered in atopic skin. Ions may play an important role in the pathology of the skin. During the wound healing process, the distribution of magnesium and calcium in the wound fluid is altered, and may activate the cell migratory response. The process of the present invention should play an important role in elucidating these disease mechanisms, especially since this is the simplest and most inexpensive method for visual imaging of ion distribution in tissue.

What I claim is:

1. A method of producing a visual image of ions in a tissue sample comprising the steps of:
   (a) preparing a frozen tissue sample;
   (b) placing the frozen tissue sample in contact with a thin membrane comprising a water soluble gel or plastic thin film, said thin membrane having a fluorescent or color ion indicator thereon, which becomes incorporated into or forms a film on the thin frozen tissue sample and fluoresces or changes color under light of a particular wavelength; and
   (c) subjecting the frozen tissue sample on the thin membrane from step (b) to light having a wavelength to cause the ion indicator to fluoresce or change color.

2. The method of claim 1, wherein the thin frozen tissue sample is human skin.

3. The method of claim 2, wherein the thin frozen tissue sample is a cross-section of human skin.

4. The method of claim 1, wherein the thin frozen tissue sample is non-dried tissue from about 5 to 10 $\mu$m thick.

5. The method of claim 1, wherein the thin frozen tissue sample is non-dried tissue cut with a cryostat to a thickness of from about 5 to 10 $\mu$m.

6. The method of claim 1, wherein step (c) is carried out in a fluorescent microscope, confocal microscope, optical microscope or multiphoton laser scanning microscope.

7. The method of claim 1, wherein ions to be detected in the tissue sample are selected from the group consisting of calcium, magnesium, potassium, sodium, zinc, chlorine, active oxygen, nitrogen oxide and, intracellular electric potential and lipids.

8. The method of claim 1, wherein the ion indicator fluoresces only at particular wavelengths in the presence of a specific ion.

9. The method of claim 1, wherein the membrane comprises water, a polymer and said ion indicator.

10. The method of claim 9, wherein the membrane comprises about 2 wt % of said polymer and about 98 wt % water.

11. The method of claim 10, wherein the polymer is selected from the group consisting of polyacrylamide, polyvinyl alcohol, polysaccharide which is gelated or solidified into sheet form by cross-bridging or drying, or crosslinking or polymerization of a monomer.

12. The method of claim 11, wherein the membrane forms a three-dimensional structure which prevents water flow inside the structure so as to prevent any substantial movement of the ion indicator in the membrane.

13. The method of claim 1, wherein the thin frozen tissue sample is about 7 $\mu$m thick human epidermis.

14. A method of producing a visual image of hydrogen ions in a tissue sample comprising the steps of:
   (a) preparing a thin frozen tissue sample;
   (b) placing the thin frozen tissue sample in contact with a thin membrane upon which a hydrogen ion indicator has been incorporated; and
   (c) subjecting the thin frozen tissue sample on the thin membrane from step (b) to light having a visible wavelength to cause the hydrogen ion indicator to change color.

15. The method of claim 14, wherein the thin membrane comprises water, a hydrogen ion indicator and a water soluble polymer selected from the group consisting of polyacrylamide, polyvinyl alcohol, polysaccharide which is gelated or solidified into sheet form by cross-bridging or drying, or crosslinking or polymerization of a monomer.

16. The method of claim 15, wherein the hydrogen ion indicator is ethanol which has been applied to the surface of the membrane.

17. The method of claim 15, wherein the thin membrane is in the form of a gel and comprises about 2% of a water soluble polymer.

18. A method of producing a visual image of ions in a tissue sample comprising the steps of:
   (a) preparing a frozen tissue sample;
   (b) placing the frozen tissue sample in contact with a thin membrane comprising a water soluble polymer gel or plastic thin film, said thin membrane having a fluorescent or color ion indicator thereon, which becomes incorporated into or forms a film on the thin frozen tissue sample and fluoresces or changes color under light of a particular wavelength; and
   (c) subjecting the thin frozen tissue sample on the thin membrane from step (b) to light having a wavelength to cause the ion indicator to fluoresce or change color to enable detection of ions in the tissue sample,
   wherein ions to be detected in the tissue sample are selected from the group consisting of calcium, magnesium, potassium, sodium, zinc, chlorine, active oxygen, nitrogen oxide and intracellular electric potential and lipids.

* * * * *